United States Patent [19]

Aasen et al.

[11] Patent Number: 4,871,786

[45] Date of Patent: Oct. 3, 1989

[54] ORGANIC FLUORIDE SOURCES

[75] Inventors: Steven M. Aasen; Joel D. Oxman; F. Andrew Ubel, III, all of St. Paul, Minn.

[73] Assignee: Minnesota Mining and Manufacturing Company, St. Paul, Minn.

[21] Appl. No.: 252,530

[22] Filed: Oct. 3, 1988

[51] Int. Cl.$^4$ ............................................. C08K 5/49
[52] U.S. Cl. ................................... 523/113; 523/114; 523/115; 523/116; 523/118; 523/120; 523/122; 524/184; 524/185; 524/507; 524/525; 524/560; 424/423; 424/424; 424/435; 424/487; 424/52
[58] Field of Search ............... 523/113, 114, 115, 116, 523/118, 120, 122; 524/184, 185, 507, 525, 560; 424/423, 424, 435, 487

[56] References Cited

U.S. PATENT DOCUMENTS

| | | | |
|---|---|---|---|
| 2,824,083 | 2/1958 | Parry et al. | 528/91 |
| 2,980,733 | 4/1961 | Sowa | 64/8 |
| 3,341,505 | 9/1967 | Gander | 526/287 |
| 3,969,499 | 7/1976 | Lee et al. | 424/52 |
| 4,469,674 | 9/1984 | Shah et al. | 424/52 |
| 4,515,910 | 5/1985 | Rawls et al. | 523/115 |
| 4,772,325 | 9/1988 | Kwan et al. | 106/35 |

OTHER PUBLICATIONS

J. Dent. Res. 1987, 66, 1591 (Tanaka, et al.) p. 2, lines 23-25, Caries Res. 1983, 17, 32 (Rawls, et al.).

*Primary Examiner*—John Kight
*Assistant Examiner*—S. A. Acquah
*Attorney, Agent, or Firm*—Donald M. Sell; Walter N. Kirn; Robert W. Sprague

[57] ABSTRACT

Organic fluoride sources comprising a tetrafluoroborate salt and capable of releasing fluoride ions into dentition in order to provide inhibition and/or prevention of dental caries are disclosed. A method of releasing fluoride ion into dental tissue is also disclosed.

22 Claims, No Drawings

ORGANIC FLUORIDE SOURCES

TECHNICAL FIELD

The present invention relates to compositions which are capable of releasing fluoride ions. More specifically, this invention relates to dental compositions and articles which contain an organic-soluble fluoride source(s) and are capable of releasing fluoride ion into the surrounding tissue. Further, the invention relates to a method of inhibiting the progression of and/or preventing dental caries.

BACKGROUND OF THE INVENTION

The use of fluoride ion in the dental industry to treat teeth for the prevention and/or inhibition of dental decay is well known. Until recent years, primarily inorganic fluoride salts, such as sodium fluoride, have been utilized as the fluoride ion source not only in rinses, toothpastes and fluorides treatments, but also in dental composites, sealants, adhesives and the like. In regard to these latter materials, the inorganic fluoride salt is suspended in any suitable monomeric or polymeric system and fluoride ion release is accomplished by a diffusion/dissolution mechanism. Such suspensions are difficult to maintain, i.e., the inorganic salt tends to settle and/or separate, and often require repeated mixing or shaking by the user to ensure a homogeneous blend. The subsequent dissolution of a particle of salt in the polymerized article is also a concern, since this may compromise the performance of the composite.

U.S. Pat. No.3,341,505 discloses a film-forming composition which is the polymerization product of an acrylate or methacrylate-functional amine-containing monomer, which is typically reacted with an appropriate acid to form a halide, sulfate or sulfonate salt, and acrylates or methacrylates of alkyl alcohols containing 1 to 12 carbon atoms. These compositions are used as flexible water-soluble films on the skin or as cement compositions for adhering bandages to the skin.

U.S. Pat. No. 4,515,910 discloses a fluoride-releasing interpolymer which is the reaction product of a monomer bearing an anion-exchange site carrying fluoride ions (for example, a quaternary ammonium fluoride), a copolymerizable alkyl acrylate or methacrylate monomer of about 12 carbon atoms and a crosslinking monomer. This composition is disclosed as having utility as a sealant or restorative dental material, as a removable oral device for delivering fluoride and as a bone cement in bio-medical applications.

There is disclosed in International Application PCT/US82/00695 a dental composition comprising a controlled-release fluoride source which comprises a complex of a fluoride-containing Lewis acid and a Lewis base. The preferred Lewis acid is $BF_3$ and the Lewis base portion of the complex may be, inter alia, an amine capable of free radical polymerization with the other prepolymeric material of the composition.

M. Tanaka, et al, J. Dent. Res. 1987, 66, 1591, describes a fluoride-releasing methacryloyl fluoridemethyl methacrylate copolymer used as a dental sealant.

SUMMARY OF THE INVENTION

The invention provides a novel polymerizable composition which releases fluoride to dental tissue and which comprises one or more polymerizable monomers and, as a fluoride source, an organic compound comprising one or more tetrafluoroborate salt moieties, the cations of which are selected from the group consisting of quaternary ammonium, iodonium, sulfonium and phosphonium, the organic compound being capable of providing fluoride to the surrounding tissue, and being present in the polymerizable composition in an amount sufficient to inhibit and/or prevent dental caries, and being substantially soluble in and/or polymerizable with the polymerizable monomers.

The polymerizable compositions release fluoride to tissue in the mouth by virtue of the presence of tetrafluoroborate ion. The tetrafluoroborate is included in the form of a salt of an organic compound, which salt is substantially soluble in and/or polymerizable with the polymerizable monomers. This salt is referred to herein as an organic fluoride source or simply as a fluoride source. When the fluoride source is polymerizable with the polymerizable monomers, the composition so obtained retains the properties required of dental restorative compositions despite the presence of the additional component. Likewise, a suitable composition obtains when the organic compound is not polymerizable with the polymerizable monomers. Polymerizable fluoride sources are advantageous in that methods of preparing them are versatile. Thus, their structure may be tailored to any of a number of specific uses. It is necessary, however, to match the reactivity of the polymerizable fluoride sources (their mode of polymerization) to the reactivities of the polymerizable monomers of the composition.

Non-polymerizable fluoride sources, on the other hand, do not require such matching of reactivity. Thus, they are advantageous in that they are compatible with virtually any polymerizable monomer irrespective of the mode of polymerization. Regardless of whether the organic compound is polymerizable or not, the compositions of the invention remain homogeneous for prolonged periods and provide cured materials which release fluoride without creating voids in the cured material.

The compositions of the invention demonstrate utility in dental applications where it is desirable to provide fluoride release into dentition. The specific areas of application include, but are not limited to, sealants, adhesives, bases, luting cements, orthodontic cements and composites, and articles comprised thereof such as caps, crowns, bridges, fillings, orthodontic appliances and removable prosthetic devices.

DETAILED DESCRIPTION OF THE INVENTION

The compositions of the invention employ one or more substantially soluble organic compounds which serve as fluoride sources by virtue of incorporation of tetrafluoroborate. When referring to the organic fluoride source, the term "substantially soluble" for present purposes is meant to indicate that the fluoride source is soluble to the extent that an amount of fluoride source effective to inhibit the progression of and/or prevent dental caries will dissolve in the polmerizable monomers of the compositions. The fluorides source may be incapable of polymerization with the polymerizable monomers also present in the compositions, or the fluoride source may actually be polymerizable with the polymerizable monomers. The preferred non-polymerizable organic fluoride sources are compounds of Formula I below:

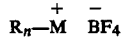

$$R_n{-}M^+ \quad BF_4^- \qquad \text{I}$$

wherein M is I, N, P or S; n is 2 when M is I, n is 3 when M is S, and n is 4 when M is N or P; and each R group is independently selected from the group consisting of straight chain or branched chain alkyl of 1 to about 12, preferably 1 to about 8, carbon atoms; substituted straight chain or branched chain alkyl of 1 to about 12, preferably 1 to about 8, carbon atoms; phenyl; and substituted phenyl, with the proviso that when R is substituted alkyl or substituted phenyl, there are 1 to 2 substituents selected independently from the group consisting of straight chain or branched chain alkyl or akkoxy of 1 to about 8, preferably 1 to about 4, carbon atoms, halogen, phenyl, amino, mono- or dialkyl amino wherein the alkyl group(s) is straight chain or branched chain of 1 to about 8, preferably 1 to about 4 carbon atoms, mercapto and a moiety of the formula

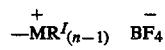

$$-MR^I{}_{(n-1)}^+ \quad BF_4^-$$

wherein M and n are as defined above and each $R^I$ group is independently selected from the group consisting of straight chain or branched chain alkyl of 1 to about 12, preferably 1 to about 8 carbon atoms; substituted straight chain or branched chain alkyl of 1 to about 12, preferably 1 to about 8 carbon atoms; phenyl; and substituted phenyl, with the proviso that when $R^I$ is substituted alkyl or substituted phenyl, there are 1 or 2 substituents selected independently from the group consisting of straight chain or branched chain alkyl or alkoxy of 1 to about 8, preferably 1 to about 4 carbon atoms, halogen, amino, mono-or dialkyl amino wherein the alkyl group(s) is straight chain or branched chain alkyl of 1 to about 8, preferably 1 to about 4 carbon atoms, and mercapto. Unsubstituted alkyl and phenyl as R groups are preferred. Most preferred are compounds of Formula I wherein all R groups are unsubstituted straight chain alkyl of 1 to about 8 carbon atoms.

Preferred polymerizable fluoride sources are compounds of Formula II below:

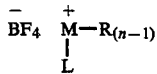

$$BF_4^- \quad \underset{L}{M^+{-}R_{(n-1)}} \qquad \text{II}$$

wherein R, M and n are defined as above in the context of Formula I, and L is an organic ligand comprising a moiety capable of polymerization via a cationic, condensation or preferably a free radical mechanism. Polymerizable fluoride sources preferably are substantially soluble in the polymerizable monomers.

The organic fluoride sources therefore comprise ammonium, iodonium, sulfonium or phosphonium cations. The anion is tetrafluoroborate. The compounds are capable of releasing fluoride in the presence of hydroxylic solvents such as water, alcohols and/or organic acids.

Non-polymerizable fluoride sources are preferred by virtue of their compatibility with virtually any polymerization monomer. Quaternary ammonium salts are preferred to iodonium, phosphonium or sulfonium salts. Among the most preferred non-polymerizable compounds are tetramethylammonium tetrafluoroborate, tetraethylammonium tetrafluoroborate, tetrapropylammonium tetrafluoroborate, tetrabutylammonium tetrafluoroborate and benzyltriethylammonium tetrafluoroborate. These compounds are commercially available, and they also are easily prepared by conventional methods, for example, via quaternization of an appropriate tertiary amine and anion exchange to provide the tetrafluoroborate salt.

The non-polymerizable sulfonium or phosphonium salts useful in the compositions of the invention are prepared by conventional methods in a manner analogous to the preparation of quaternary ammonium salts, for example, by alkylation of an appropriate sulfide or tertiary phosphine and subsequent anion exchange to provide the tetrafluoroborate salt.

A non-polymerizable organic fluoride source or a mixture of non-polymerizable organic fluoride sources is incorporated in the compositions of the invention in an amount effective to prevent and/or inhibit dental caries. A preferred range is from about 1 percent by weight relative to the total weight of the polymerizable monomer in the composition to the solubility limit of the fluoride source in the particular composition. This range is generally suitable, but the precise amount of soluble organic fluoride source employed or article in which it is incorporated. The most preferred range for compositions intended for use as a dental restorative composition, a dental sealant, a dental adhesive, a base, a luting cement, an orthodontic cement or a prosthetic device is from 1 to about 10 percent by weight relative to the total weight of the polymerizable monomer in the composition. Further, amounts of the fluoride source greater than the solubility limit for a given composition may be employed as a suspension, but with the concommitant disadvantages inherent in a suspension as described above in connection with, for example, compositions containing sodium fluoride.

In general, as the number of carbon atoms in the R groups of the organic fluoride source is increased, the organic solubility is increased. Greater solubility is generally more favorable, as larger amounts of fluoride can be made available to the tooth in a given mass of sealant, composite, base or adhesive. The water solubility may decrease with increasing organic solubility and may slow the fluoride release from the polymer into the tooth. Therefore, a combination of several compounds may be useful in adjusting the release rate and total fluoride concentration for a particular composition. In any case, a non-polymerizable fluoride source employed in a polymerizable composition of the invention should be substantially soluble in the polymerizable monomers employed.

As discussed above, the organic fluoride source incorporated into a composition of the invention may itself be polymerizable with the polymerizable monomers of the composition. Such polymerization fluoride sources of Formula II comprise a group L which comprises a polymerizable moiety capable of free radical, cationic or condensation polymerization with the polymerizable monomers. These compounds may be prepared in many conventional ways. Several representative routes, which are not intended to limit the invention, are described below, beginning with the general route shown in Scheme I.

SCHEME I

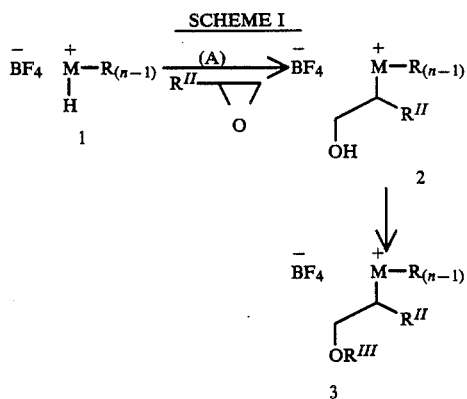

In Scheme I, M is N or P, and R and n are as defined above for compounds of Formula II, and $R^{II}$ and $R^{III}$ are as defined below. Compounds of formula 1 in Scheme I are readily prepared by addition of a commercially available tertiary amine or phosphine to an aqueous solution of fluoboric acid. Step (A) then involves reaction of a salt of formula 1 with an epoxide. While mixtures of isomers are often obtained in these reactions, only one isomer is shown for illustrative purposes. The resulting ring-opened product of formula 2 may itself serve as a polymerizable fluoride source if the polymerizable monomers of the composition are polymerizable with the pendant hydroxyl group. In such a case, a useful polymerizable monomer will comprise an electrophilic moiety such as an isocyanate, epoxide, carboxylic acid derivative such as an acyl halide, an acid anhydride, or the like which will react with (and is therefore complementary to) the pendant nucleophilic hydroxyl when the compound of formula 2 is incorporated into the polymerizable monomers of the composition. Compounds of formula 2 may also serve as a polymerizable fluoride source if the group $R^{II}$ comprises a moiety polymerizable with the polymerizable monomer of the composition. Accordingly, $R^{II}$ may comprise a nucleophilic moiety such as hydroxyl, which is complementary to an appropriate electrophilic moiety in the polymerization monomer such as an epoxide, an isocyanate, or a carboxylic acid derivative such as an acyl halide, an acid anhydride or the like. Polarity may be reversed as well, with $R^{II}$ comprising an electrophilic moiety not susceptible to attack by the salt of formula 1, and the polymerizable monomer comprising a complementary nucleophile. Furthermore, compounds of formula 2 may serve as polymerizable fluoride sources if $R^{II}$ comprises a moiety such as a methacrylate, acrylate, methacrylamide, acrylamide, vinyl, vinyl ether, or other polymerizable olefinic moiety susceptible to free radical or cationic polymerization, and the polymerization monomer is complementary thereto.

If, however, the polymerizable monomer is not complementary to the pendant hydroxyl, and the group $R^{II}$ comprises no moiety complementary to the polymerizable monomers, step (B) of Scheme I serves to provide the requisite polymerizable group. In Step (B) a compound of formula 2 is reacted with an electrophilic compound such as an isocyanate, epoxide, a carboxylic acid derivative or the like which imparts a moiety $R^{III}$ complementary to the polymerizable monomer. Such a moiety $R^{III}$ is electrophilic, nucleophilic, or capable of free radical or cationic polymerization, with the character of the moiety being selected consistent with the nature of the polymerizable monomers to be used in the composition.

When contemplating an appropriate polymerization fluoride source/polymerizable monomer system, careful matching of the reactivity of the various components is required. While this can be done as described above, there is potential for complications when balancing the nucleophilic and electrophilic reactivity of the polymerizable fluoride source with the complementary reactivity of the polymerization monomers of the composites. Thus, preferred compositions of the invention employ polymerization fluoride sources capable of free radical polymerization in conjugation with like polymerizable monomers.

There exists alternative conventional routes by which polymerizable fluoride sources may be prepared. Scheme II below provides the same final products as Scheme I by a different series of steps.

SCHEME II

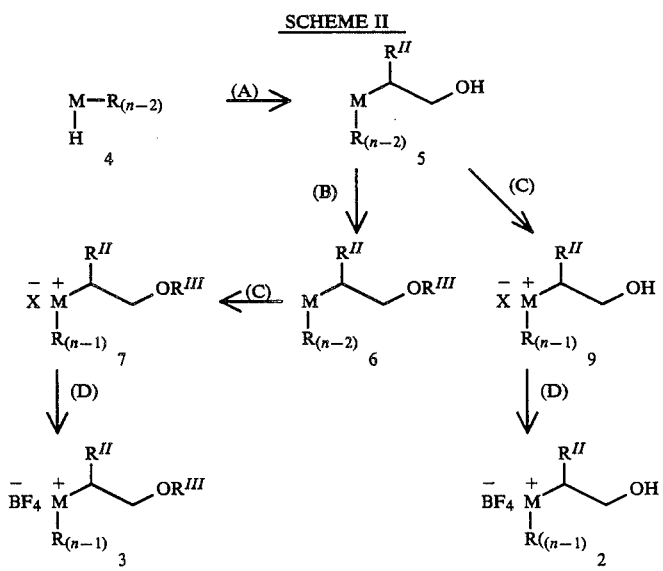

R, M, n, $R^{II}$ and $R^{III}$ are as defined above.

Step (A) of Scheme II is an acid catalyzed opening of an epoxide to afford the hydroxy compound of formula 5. Step (B) is as described for Step (B) of Scheme I, affording a compound of formula 6. The compound of formula 6 is then alkylated in Step (C) by an appropriate alkyl halide, preferably an alkyl iodide, for example iodomethane, to provide a compound of formula 7. In Step (D), anion exchange of the halide for tetrafluoroborate is carried out with silver tetrafluoroborate to provide a compound of formula 3. Alternatively, Steps (C) and (D) may be carried out on the compounds of formulas 5 and 9 respectively if, as discussed above, $R^{II}$ comprises the appropriate polymerizable moiety or if the hydroxyl group is an appropriate moiety for polymerization with the polymerization monomer.

A final illustrated alternative preparation of polymerizable fluoride sources is shown in Scheme III.

SCHEME III

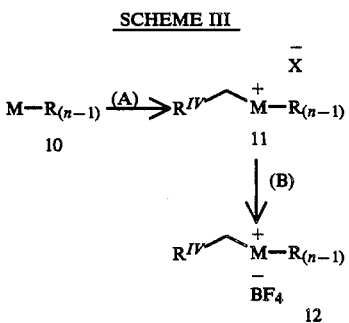

Again, R, n, and M are as defined above, and $R^{IV}$ is an organic ligand comprising a polymerizable moiety, also as discussed above. Step (A) of Scheme III is an alkylation of the starting species of formula 10 with a primary organic halide which also comprises a polymerizable moiety to afford a halide salt of formula 11. The compound of formula 11 is then treated in Step (B) with $AgBF_4$ to afford a polymerizable fluoride source of formula 12. Alternatively, a compound of formula 10 may be alkylated with a compound which does not comprise a polymerizable moiety, but rather comprises a latent polymerizable moiety or some functionality to which a polymerizable moiety may be attached in a subsequent step.

As with the non-polymerizable fluoride sources, the polymerizable fluoride sources are incorporated in the compositions of the invention in an amount effective to prevent and/or inhibit the formation of dental caries in the neighboring biological tissue when the composition is in place in the mouth. Mixtures of polymerizable and non-polymerizable fluoride sources may be employed. The amount of organic fluoride source to be used varies according to several factors, among them the particular use of the composition and the weight percent of fluoride in the fluoride source or mixture of fluoride sources. In general, the fluoride source or mixture of fluoride sources is incorporated in the composition such that the composition contains from about 0.1 percent by weight to about 10 percent by weight, preferably 0.3 to about 5 percent by weight fluoride relative to the weight of the polymerizable monomer (exclusive of the polymerizable monomer(s) constituting the fluoride source itself) in the composition.

The polymerizable compositions of the invention comprise polymerizable monomer(s) and a fluoride source as described above. Useful polymerizable monomers (to be selected consistent with the character of the fluoride source as discussed above) include acrylate, methacrylate, urethane and epoxy resins, and mixtures and derivatives thereof. Examples of suitable polymerizable monomers are disclosed in U.S. Pat. Nos. 3,066,112, 3,539,533, 3,629,187, 3,709,866, 3,751,399, 3,736,132, 3,860,556, 4,002,669, 4,115,346, 4,259,117, 4,292,029, 4,308,190, 4,327,014, 4,379,695, 4,387,240, 4,404,150, and 4,515,930, each of which is incorporated herein by reference. Specific preferred polymerizable monomers include the diglycidyl methacrylate of bisphenol A (Bis-GMA), 2-hydroxyethyl methacrylate (HEMA), polyethyleneglycol dimethacrylate (PEGDMA) and triethyleneglycol dimethacrylate (TEGDMA).

Typically the compositions of the invention will be capable of free radical polymerization. Accordingly, they will comprise a polymerization initiation system such as an organic peroxide either alone or preferably in combination with a suitable amine, sulfide, thiol, phosphine or other such compound capable of producing radicals via reaction with the peroxide. Alternatively, the compositions may comprise a photoinitiation system such as a ketone or an alpha diketone, either alone or preferably in combination with a suitable amine, peroxide, sulfide, thiol, phosphine or other such compound capable of being sensitized by or otherwise reacting with the carbonyl compound to initiate free radical polymerization of the composition upon exposure to light.

The compositions of the invention also may comprise suitable accelerators, stabilizers, pigments, dyes, viscosity modifiers, surface tension depressants and wetting aids, antioxidants, and other suitable ingredients. Suitable fillers may be used in conjugation with the compositions of the invention to provide composites. The amount and type of any ingredient used with the compositions of the invention may be adjusted to provide the desired physical properties both before and after curing.

For evaluation of the adhesion of restorative or sealant compositions of the invention to either the dentin or enamel surface of a tooth, teeth were prepared according to the following procedure. Five bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel as appropriate. During this and subsequent grinding and polishing steps, the teeth were continuously rinsed with water. Further grinding and polishing of the teeth was carried out by first mounting Grade 320 and then Grade 600 silicon carbide paper-backed abrasive on the lapidary wheel. The polished teeth were stored in distilled water and used for testing within 2 hours after polishing. The polished teeth were removed from the water and dried using a stream of air.

For measurement of adhesion to dentin, the following technique was utilized. After the tooth preparation described above, a single drop of SCOTCHPREP TM-brand dentin primer was painted onto each of the polished tooth surfaces with a brush and allowed to stand for 60 seconds. The primer was then blown dry with a stream of air and overcoated with a layer of additional SCOTCHBOND TM 2 brand light cure dental adhesive. The adhesive was applied with a brush, blown lightly into a film with a stream of air and cured using a 20 second irradiation with a VISILUX ™ 2 brand dental curing light (available from 3M.) Previously prepared molds made from a 2 mm thick Teflon sheet with a 4 or 5 mm diameter hole through the sheet were clamped to each polished tooth so that the central axis of the hole in the mold was normal to the polished tooth surface. The hole in each mold was filled with a dental restorative (typically SILUX ™ brand restorative, universal shade, commercially available from 3M) which has been modified to contain an organic fluoride source according to the invention. The restorative was then cured using a 20 second irradiation with a VISILUX ™ 2 brand curing light.

For measurement of adhesion to enamel, the following technique was utilized. SCOTCHBOND ™ brand etching gel (commercially available from 3M) was applied to exposed enamel for 1 minute using a gentle dabbing technique. The enamel surface was then rinsed vigorously with water for 30 seconds and dried thoroughly with a stream of air. At this point the enamel appears dull-white. A previously prepared mold made from a 2 mm thick Teflon sheet with a 4 or 5 mm diameter hole through the sheet was placed over the enamel and clamped securely to each polished tooth so that the central axis of the hole in the mold was normal to the polished tooth surface. CONCISE ™ brand white sealant (available from 3M), which optionally comprises an organic fluoride source according to the invention, was then applied to the mold cavity. The sealant was cured by exposure to VISILUX ™ 2 brand curing light for a period of 20 seconds.

Following the curing of either the restorative or the sealant, the teeth and molds were allowed to stand for about 5 minutes at room temperature, then stored in distilled water at 37° C. for 24 hours. The molds were then carefully removed from the teeth, leaving a molded button of restorative or sealant attached to each tooth. Adhesive strength was evaluated by mounting the acrylic disk in a holder clamped in the jaws of an Instron apparatus with the polished tooth surface oriented parallel to the direction of pull. A loop of orthodontic wire (0.44 mm diameter) was placed around the restorative or sealant button adjacent to the polished tooth surface. The ends of the orthodontic wire were clamped in the pulling jaw of the Instron apparatus, thereby placing the bond in shear stress. The bond was stressed until failure, using a crosshead speed of 2 mm/minute. The adhesion values were calculated using the following formula:

$$\text{Adhesion in kg/cm}^2 = \frac{\text{Instron Shear Force (in kg)}}{\text{Area of the Mold (in cm}^2\text{)}}$$

The incorporation of fluoride into tooth tissue was quantitatively measured utilizing the following technique. The tooth restorative or sealant, and adhesive were cross-sectioned using a diamond saw and analysis was performed utilizing a secondary ion mass spectrometer ("SIMS", available from Perkin Elmer). The distribution of fluoride in the tooth is thereby determined as a function of depth into the dentin or enamel, thus showing the extent of incorporation of fluoride into the dentin or enamel.

The following examples are intended to illustrate the invention. They are not intended to limit the invention.

EXAMPLE 1

One hundred parts by weight of the monomer resin portion of SCOTCHBOND ™ brand dental adhesive (commercially available from 3M) described in U.S. Pat. Nos. 4,669,983 and 4,670,576, incorporated herein by reference were modified to include a fluoride source. The weight percentage of the fluoride source in the composition is indicated in Table I relative to the amount of resin. Tetraethylammonium tetrafluoroborate according to the invention, and the inorganic fluoride salts sodium fluoride and zirconium fluoride were incorporated and tested as described below to demonstrate the relative rates of leaching for the several fluoride sources. The inorganic fluoride salts were incorporated as particle suspensions, while the organic fluoride source was incorporated as a solution. The resin specimens were formed and cured into disks 20 mm in diameter and 1 mm thick.

A fluoride-selective electrode, Orion Model 96-09-00, (available from Orion Research Inc., Cambridge, Mass.) was used to quantify the amount of fluoride ion released from the polymerized specimens in water. The electrode was calibrated using dilutions of the Fluoride Activity Standard #940907, a 100 parts per million ("ppm") F standard fluid manufactured by Orion Research Inc. An experimental standard curve was generated and an equation was fitted to the experimental data and was used to quantitate the fluoride release.

A cured resin specimen was then placed in a jar of deionized water at 25° C. The fluoride probe was periodically placed in the water and the relative millivolt value was recorded. This value was converted to ppm $F^-$ by comparison to the standard curve. Micrograms of $F^-$ per gram of the cured resin specimen were then calculated and these values were reported as a function of time of storage in the water. TABLE I lists the weight percent of the fluoride source in the resin and the cumulative amount of fluoride released into water (in micrograms of $F^-$ per gram of the cured resin specimen) at 19 and 60 days.

TABLE I

| Fluoride Source | Wt. % | Total $F^-$ in the Composition (mcg/g) | Cumulative $F^-$ Release (mcg/g) 19 Days | 60 Days | Total % $F^-$ Released |
|---|---|---|---|---|---|
| Tetraethylammonium tetrafluoroborate | 2.60 | 9100 | 665 | 1262 | 13.9 |
| Sodium Fluoride | 0.50 | 2300 | 219 | 411 | 17.1 |
| Zirconium Fluoride | 2.00 | 9100 | 414 | 570 | 6.3 |

Thus it is demonstrated that a composition comprising a tetrafluoroborate salt is capable of sustained release of fluoride.

Examples 2–6

Samples for Examples 2 and 3 were made using one hundred parts by weight of the resin portion of CONCISE ™ white sealant (commercially available from 3M and described in U.S. Pat. No. 4,150,012 which is incorporated herein by reference) and tetrabutylammonium tetrafluoroborate. Examples 4, 5 and 6 were made using a resin system which contained a 55:45 weight ratio of bisphenol-A diglycidyl ether dimethacrylate ("Bis-GMA") monomer to 2-hydroxyethyl methacrylate ("HEMA") monomer, along with tetrabutylammonium tetrafluoroborate. TABLE II lists the weight percent of the fluoride source based on the weight of the resin, and the cumulative amount of fluoride released into water (in micrograms $F^-$ per gram of sample) at 60 days as determined according to the method of Example 1.

TABLE II

| Example # | Wt % of Tetrabutylammonium Tetrafluoroborate | Cumulative $F^-$ Release (mcg/g) in 60 Days |
|---|---|---|
| 2 | 4.0 | 443.2 |
| 3 | 8.0 | 536.0 |
| 4 | 2.0 | 155.4 |
| 5 | 4.0 | 374.6 |
| 6 | 8.0 | 290.1 |

EXAMPLE 7

A resin/composite material was prepared with the following formulation wherein the amounts are expressed as parts by weight:

| | | |
|---|---|---|
| 55.0 parts | Bis-GMA | |
| 45.0 | HEMA | |
| 0.25 | Camphorquinone | |
| 0.05 | 4-(Dimethylamino)phenethyl alcohol ("DMAPE") | |
| 4.00 | Tetrabutylammonium tetrafluoroborate | |
| 104.75 | $ZrO_2$—$SiO_2$ filler prepared according to U.S. Pat. No. 4,503,169, which is incorporated herein by reference | |
| 2.10 | Aerosil TM R-972 colloidal silica available from Degussa Inc., Frankfurt, Germany | |

Adhesion testing was performed on the sample according to the procedure outlined above. SCOTCH-PREP TM brand dentin primer (commercially available from 3M and disclosed in U.S. Pat. No. 4,719,149, incorporated herein by reference) was applied to the dentin. After 60 seconds, the primer was blown dry with air, and a Teflon mold was placed above the dentin. The resin/composite material was placed in the mold and cured with a VISILUX TM 2 brand light for 20 seconds. The samples were stored in water overnight and shear adhesion values were obtained the following day. The mean experimental shear adhesion value obtained was 185 kg/cm$^2$ with a standard deviation of 20 kg/cm$^2$.

Fluoride release from the sample was measured as described in Example 1. At 116 days cumulative $F^-$ release was 112 mcg/g; at 299 days, cumulative fluoride release was 172 mcg/g.

This example illustrates a composite/restorative material with fluoride releasing capability and good adhesion to dentin.

EXAMPLE 8

An adhesive material was prepared with the following formulation wherein the amounts are expressed as parts by weight:

| | | |
|---|---|---|
| 55.0 parts | Bis-GMA | |
| 45.0 | HEMA | |
| 0.25 | Camphorquinone | |
| 0.50 | DMAPE | |
| 4.00 | Tetrabutylammonium tetrafluoroborate | |

The adhesive material was placed on a dentin surface as described in Example 7. In order to measure the amount of fluoride incorporated into the tooth tissue, the tooth and adhesive were cross-sectioned using a diamond saw and analyzed using a secondary ion mass spectrometer (SIMS). In this experiment, a 6000 series PHI TM-profiler (available from Perkin-Elmer) was employed. An adhesive and tooth sample with no incorporated fluoride source was used as a baseline control. The $F^-$ and $O_2^-$ as 'counts' from the SIMS analysis as well as the ratio of $F^-/O_2^-$ are provided in TABLE III.

TABLE III

| Distance Beneath Surface of Dentin (microns) | $F^-$ (counts) | $O_2^-$ (counts) | $F^-/O_2^-$ |
|---|---|---|---|
| 0 | 5712 | 81 | 70.52 |
| 10 | 4937 | 179 | 27.52 |
| 20 | 4738 | 299 | 15.85 |
| 30 | 3240 | 501 | 6.47 |
| 40 | 2515 | 751 | 3.35 |
| 50 | 2148 | 956 | 2.25 |
| 75 | 3248 | 1973 | 1.65 |
| 100 | 4125 | 2795 | 1.48 |
| 125 | 2681 | 1819 | 1.47 |
| 150 | 2162 | 2675 | 0.81 |
| 200 | 1420 | 2257 | 0.63 |
| 500 | 367 | 730 | 0.50 |
| Control | 409 | 871 | 0.47 |

The data show the presence of fluoride in amounts greater than background levels. Thus, it is demonstrated that fluoride from the composition penetrates the dentin and is incorporated into it.

EXAMPLE 9

A sealant material was prepared with the following formulation wherein the amounts are expressed as parts by weight:

| | | |
|---|---|---|
| 50 parts | Bis-GMA | |
| 50 | Triethyleneglycol dimethacrylate | |
| 0.25 | Camphorquinone | |
| 0.50 | DMAPE | |
| 0.87 | $TiO_2$ | |
| 6.00 | Aerosil ® R-972 | |
| 10.00 | Tetrabutylammonium tetrafluoroborate | |

The prepared sealant material was placed on an enamel surface as described above. In order to measure the amount of fluoride incorporated into the tooth tissue, the tooth and sealant were cross-sectioned using a diamond saw and analyzed using the SIMS with a PHI TM profiler as detailed in Example 8. A sealant and tooth sample with no incorporated fluoride ion source was used as a baseline control. The $F^-$ and $O_2^-$ as 'counts' from the SIMS analysis as well as the ratio of $F^-/O^-_2$ are provided in TABLE IV.

TABLE IV

| Distance Beneath Surface of Enamel (microns) | $F^-$ (counts) | $O_2^-$ (counts) | $F^-/O_2^-$ |
|---|---|---|---|
| 0 | 108707 | 3435 | 31.7 |
| 10 | 143935 | 5187 | 27.8 |
| 20 | 178267 | 7438 | 24.0 |
| 30 | 66689 | 5651 | 11.8 |
| 40 | 7801 | 460 | 17.0 |
| 50 | 813 | 70 | 11.6 |
| 60 | 505 | 33 | 15.3 |
| 70 | 538 | 79 | 6.8 |
| 150 | 173 | 33 | 5.2 |
| Control | | | <1 |

The data show the presence of fluoride in amounts greater than background levels. Thus it is demonstrated that fluoride from the composition penetrates and is incorporated into the enamel.

EXAMPLE 10

An aqueous solution of fluoboric acid was cooled in an ice bath. Triethylamne (1 equivalent) was added dropwise with stirring. The water was then removed at reduced pressure and the resulting solid was azeotroped dry with acetone. A solution was prepared by dissolving 20 mmol of the resulting dry triethylammonium tetrafluoroborate in 30 ml of acetone. A solution of 1,4-butanediol diglycidyl either (10 mmol in 30 ml of 1:1 acetone:methylene chloride) was added with stirring. The solvent was removed at reduced pressure to afford a mixture of diols. This mixture was dissolved in 50 ml $CH_2 Cl_2$, and 20 mmol of isocyanatoethylmethacrylate was added with stirring. The resulting mixture was stirred for 20 min., and the solvent was removed at reduced pressure to afford a waxy residue. Nuclear magnetic resonance analysis of the product was consistent with a product comprising all possible isomers from the reactions.

EXAMPLE 11

According to the method of Example 10, a polymerizable fluoride source was prepared using, in place of 1,4-butanediol diglycidyl ether, 2,2-bis-(4-hydroxyphenyl)propane diglycidyl ether. Nuclear magnetic resonance analysis of the product was consistent with a product comprising all possible isomers from the reactions.

EXAMPLE 12

According to the method of Example 10 a polymerizable fluoride source was prepared using, in place of 1,4-butanediol diglycidyl ether, 2,2-bis-(4-hydroxycyclohexyl)propane diglycidyl ether. Nuclear magnetic resonance analysis of the product was consistent with a product comprising all possible isomers from the reactions.

EXAMPLE 13

Polymerizable compositions were prepared by incorporating the fluoride sources of Examples 10, 11 and 12 into mixtures of Bis-GMA and TEGDMA and adding small quantities of camphorquinone and DMAPE as photoinitiators. The compositions comprised the following ingredients with amounts being expressed as parts by weight:

| Sample A | |
|---|---|
| Fluoride source of Example 10 | 7.30 |
| Bis-GMA | 50 |
| TEGDMA | 50 |
| Camphorquinone | 0.27 |
| DMAPE | 0.54 |
| Sample B | |
| Fluoride Source of Example 11 | 14.87 |
| Bis-GMA | 50 |
| TEGDMA | 50 |
| Camphorquinone | 0.29 |
| DMAPE | 0.58 |
| Sample C | |
| Fluoride source of Example 12 | 11.98 |
| Bis-GMA | 50 |
| TEGDMA | 50 |
| Camphorquinone | 0.28 |
| DMAPE | 0.28 |

Each of these compositions was formed and cured into a disk 1 mm thick and 20 mm in diameter. The disk were then tested for fluoride released according to the method of Example 1. Fluoride release data after 116 days and 299 days in water are shown in TABLE V.

TABLE V

| Sample | Cumulative $F^-$ Release (mcg/g) | | Concentration in Sample (mcg/g) | % $F^-$ Released at | |
|---|---|---|---|---|---|
| | 116 days | 299 days | | 116 days | 299 days |
| A | 475 | 713 | 12211 | 3.89 | 5.84 |
| B | 774 | 948 | 19725 | 3.92 | 4.81 |
| C | 713 | 987 | 16164 | 4.41 | 6.11 |

This example demonstrates that prolonged fluoride release can be obtained from polymerizable fluoride sources.

EXAMPLE 14

Polymerizable compositions were prepared comprising the following ingredients with amounts expressed as parts by weight:

| Sample D | |
|---|---|
| Bis-GMA | 44.5 |
| TEGDMA | 55.5 |
| Camphorquinone | 0.28 |
| DMAPE | 0.56 |
| Inorganic filler | 744 |
| Sample E | |
| Fluoride source of Example 10 | 11.1 |
| Bis-GMA | 44.5 |
| TEGDMA | 55.5 |
| Camphorquinone | 0.28 |
| DMAPE | 0.56 |
| Inorganic Filler | 744 |
| Sample F | |
| Fluoride source of Example 11 | 11.1 |
| Bis-GMA | 44.5 |
| TEGDMA | 55.5 |
| Camphorquinone | 0.28 |
| DMAPE | 0.56 |
| Inorganic Filler | 744 |
| Sample G | |
| Fluoride source of Example 12 | 11.1 |
| Bis-GMA | 44.5 |
| TEGDMA | 55.5 |
| Camphorquinone | 0.28 |
| DMAPE | 0.56 |
| Inorganic Filler | 744 |

The inorganic filler is a mixture of 90 parts $ZrO_2$/$SiO_2$ filler with average particle size of 1.5 microns and 10 parts OX-50 fumed silica. Both fillers were treated with A-174 silane (available from Union Carbide). The compositions D-G were formed and cured into modulus bars and tested for elastic modulus according to the procedure of ISO 4049. Table VI shows the elastic modulus data. Fluoride release from the modulus bars was measured as described in Example 1. Cumulative fluoride release at 184 days is also listed in Table VI.

TABLE VI

| Sample | Elastic Modulus (GPa) | F⁻ release (mcg/g) |
|---|---|---|
| D | 7.8 | — |
| E | 6.2 | 106 |
| F | 7.9 | 55 |
| G | 8.2 | 65 |

The composites of the invention exhibit elastic modulus values comparable to the control Sample D, and release fluoride as well.

The claimed invention is:

1. A polymerizable composition which releases fluoride to dental tissue and which comprises one or more polymerizable monomers and, as a fluoride source, an organic compound comprising one or more tetrafluoroborate salt moieties, the cations of which are selected from the group consisting of quaternary ammonium, iodonium, sulfonium and phosphonium, the fluoride source being capable of providing fluoride to the surrounding tissue, and being present in the polymerizable composition in an amount sufficient to inhibit the progression of and/or prevent dental caries, and being substantially soluble in and/or polymerizable with the polymerizable monomer.

2. A polymerizable composition according to claim 1 wherein the fluoride source is non-polymerizable with the polymerizable monomer(s).

3. A polymerizable composition according to claim 2, wherein the fluoride source is of the formula

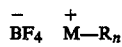

wherein M is I, N, P or S; n is 2 when M is I, n is 3 when M is S, and n is 4 when M is N or P; and each R group is independently selected from the group consisting of straight chain or branched chain alkyl of 1 to about 12 carbon atoms; substituted straight chain or branched chain alkyl of 1 to about 12 carbon atoms; phenyl; and substituted phenyl, with the proviso that when R is substituted alkyl or substituted phenyl, there are 1 or 2 substituents selected independently from the group consisting of straight chain or branched chain alkyl or alkoxy of 1 to about 8 carbon atoms, halogen, phenyl, amino, mono- or dialkyl amino wherein the alkyl group(s) is straight chain or branched chain of 1 to about 8 carbon atoms, mercapto and a moiety of the formula

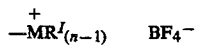

wherein M and n are as defined above and each R$^I$ group is independently selected from the group consisting of straight chain or branched chain alkyl of 1 to about 8 carbon atoms; substituted straight chain or branched chain alkyl of 1 to about 8 carbon atoms; phenyl; and substituted phenyl, with the proviso that when R$^I$ is substituted alkyl or substituted phenyl, there are 1 or 2 substituents selected independently from the group consisting of straight chain or branched chain alkyl or alkoxy of 1 to about 8 carbon atoms, halogen, amino, mono- or dialkyl amino wherein the alkyl group(s) is straight chain or branched chain alkyl of 1 to about 8 carbon atoms, and mercapto.

4. A polymerizable composition according to claim 3, wherein the fluoride source comprises a quaternary ammonium tetrafluoroborate moiety.

5. A polymerizable composition according to claim 4, wherein the fluoride source is selected from the group consisting of tetramethylammonium tetrafluoroborate, tetraethylammonium tetrafluoroborate, tetrapropylammonium tetrafluoroborate, tetrabutylammonium tetrafluoroborate, and benzyltriethylammonium tetrafluoroborate.

6. A polymerizable composition according to claim 1, wherein the fluoride source is polymerizable with the polymerizable monomer(s).

7. A polymerizable composition according to claim 6, wherein the fluoride source and the polymerizable monomer each comprise an olefinic moiety capable of free radical polymerization.

8. A polymerizable composition according to claim 7, wherein the olefinic moiety is in the form of a methacrylate moiety.

9. A polymerizable composition according to claim 7, wherein the olefinic moiety is in the form of an acrylate moiety.

10. A polymerizable composition according to claim 7, wherein the fluoride source comprises at least one quaternary ammonium tetrafluoroborate moiety.

11. A polymerizable composition according to claim 6, wherein the fluoride source is of the formula

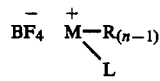

wherein M is I, N, P or S; n is 2 when M is I, n is 3 when M is S, and n is 4 when M is N or P; L is an organic liquid capable of polymerization via a cationic, condensation or free radical mechanism and each R group is independently selected from a group consisting of straight chain or branched chain alkyl of 1 to about 12 carbon atoms; substituted straight chain or branched chain alkyl of 1 to about 12 carbon atoms; phenyl; and substituted phenyl, with the proviso that when R is substituted alkyl or substituted phenyl, there are 1 or 2 substituents selected independently from the group consisting of straight chain or branched chain alkyl or alkoxy of 1 to about 8 carbon atoms, halogen, phenyl, amino, mono- or dialkyl amino erein the alkyl group(s) is straight chain or branched chain of 1 to about 8 carbon atoms, mercapto and a moiety of the formula

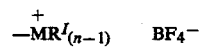

wherein M and n are as defined above and the R$^I$ groups are independently selected from the group consisting of straight chain or branched chain alkyl of 1 to about 8 carbon atoms; substituted straight chain or branched chain alkyl of 1 to about 8 carbon atoms; phenyl; and substituted phenyl, with the proviso that when R$^I$ is substituted alkyl or substituted phenyl, there are 1 or 2 substituents selected independently from the group consisting of straight chain or branched chain alkyl or alkoxy of 1 to about 8 carbon atoms, halogen, amino, mono- or dialkyl amino wherein the alkyl group(s) is straight chain or branched chain alkyl of 1 to about 8 carbon atoms, and mercapto.

12. A polymerizable composition according to claim 7, wherein the fluoride source comprises a reaction product of (i) isocyanatoethylmethacrylate; and (ii) the reaction product of triethylammonium tetrafluoroborate and 1,4-butanediol diglycidyl ether.

13. A polymerizable composition according to claim 7, wherein the fluoride source comprises a reaction product of (i) isocyanatoethylmethacrylate; and (ii) the reaction product of triethylammonium tetrafluoroborate and 2,2-bis-(4-hydroxyphenyl) propane diglycidyl ether.

14. A polymerizable composition according to claim 7, wherein the fluoride source comprises a reaction product of i) isocyanatoethylmethacrylate, and ii) the reaction product of triethylammonium tetrafluoroborate and 2,2-bis-(4-hydroxycyclohexyl)propane diglycidyl ether.

15. A polymerizable composition according to claim 1 in the form of a dental restorative composition, a dental sealant, a dental adhesive, a base, a luting cement, or an orthodontic cement.

16. A polymerized article prepared from a polymerizable composition according to claim 1.

17. A method of inhibiting the progression of and/or preventing dental caries in a mammal which method comprises (i) applying a composition according to claim 1 to a site in the mouth of the mammal; (ii) polymerizing the composition; and (iii) allowing the polymerized composition to remain in the mouth for a time sufficient to inhibit the progression of and/or prevent dental caries through release of fluoride to the tissue of the mouth of the mammal.

18. A method of inhibiting the progression and/or preventing dental caries in a mammal, which method comprises (i) placing in the mouth of the mammal a polymerized article which is prepared from a composition according to claim 1; and (ii) allowing the article to remain in the mouth of the mammal for a time sufficient to inhibit the progression of and/or prevent dental caries through the release of fluoride to the tissue of the mouth of the mammal.

19. A method of inhibiting the progression and/or preventing dental caries in a mammal, which method comprises (i) applying a composition according to claim 3 to a site in the mouth of the mammal; (ii) polymerizing the composition; ;and (iii) allowing the polymerized composition to remain in the mouth of the mammal for a time sufficient to inhibit the progression of and/or prevent dental caries through release of fluoride to the tissue of the mouth of the mammal.

20. A method of inhibiting the progression of and/or preventing dental caries in a mammal, which method comprises i) applying a composition according to claim 6 to a site in the mouth of the mammal; ii) polymerizing the composition; and iii) allowing the polymerized composition to remain in the mouth of the mammal for a time sufficient to inhibit the progression of and/or prevent dental caries through release of fluoride to the tissue of the mouth of the mammal.

21. A method of inhibiting the progression of and/or preventing dental caries in a mammal, which method comprises (i) placing in the mouth of the mammal a polymerized article which is prepared from a composition according to claim 3; and (ii) allowing the article to remain in the mouth of the mammal for a time sufficient to inhibit the progression of and/or prevent dental caries through the release of fluoride to the tissue of the mouth of the mammal.

22. A method of inhibiting the progression of and/or preventing dental caries in a mammal, which method comprises (i) placing in the mouth of the mammal a polymerized article which is prepared from a composition according to claim 6; and (ii) allowing the article to remain in the mouth of the mammal for a time sufficient to inhibit the progression of and/or prevent dental caries through the release of fluoride to the tissue of the mouth of the mammal.

* * * * *

UNITED STATES PATENT AND TRADEMARK OFFICE
CERTIFICATE OF CORRECTION

PATENT NO. : 4,871,786
DATED : October 3, 1989
INVENTOR(S) : Steven M. Aasen, Joel D. Oxman, F. Andrew Ubel, III It is certified that error appears in the above-identified patent and that said Letters Patent is hereby corrected as shown below:

Col. 1, line 20, "fluorides" should read ---fluoride---

Col. 2, line 62, "fluorides" should read ---fluoride---

Col. 3, line 15, "akkoxy" should read ---alkoxy---

Col. 5, last line, "polymerization" should read ---polymerizable---

Col. 3, line 63, "polymerization" should read ---polymerizable---

Col. 6, line 11, "and the polymerization" should read --and the polymerizable--

Col. 6, line 27, "polymerization" should read ---polymerizable---

Col. 6, line 34, "polymerization" should read ---polymerizable---

Col. 7, line 15, "the polymerization" should read ---the polymerizable---
         polymerizable---

Col. 16, line 39, "from a group" should read ---from the group---

Col. 16, line 48, "erein" should read ---wherein---

Signed and Sealed this

Twenty-second Day of January, 1991

*Attest:*

HARRY F. MANBECK, JR.

*Attesting Officer*         *Commissioner of Patents and Trademarks*